US00PP32140P3

(12) United States Plant Patent
Koie et al.

(10) Patent No.: US PP32,140 P3
(45) Date of Patent: Sep. 1, 2020

(54) HOP PLANT NAMED 'FURANO 1501U GO'

(50) Latin Name: ***Humulus lupulus* L.**
Varietal Denomination: Furano 1501U Go

(71) Applicant: Sapporo Breweries Limited, Shibuya-ku, Tokyo (JP)

(72) Inventors: Koichiro Koie, Kamifurano-cho (JP); Yutaka Itoga, Kamifurano-cho (JP); Mitsuhiro Uemoto, Kamifurano-cho (JP); Yasunori Arai, Asahikawa (JP); Masanobu Goto, Kamifurano-cho (JP); Seigi Kuji, Kamifurano-cho (JP)

(73) Assignee: Sapporo Breweries Limited, Tokyo (JP)

( * ) Notice: Subject to any disclaimer, the term of this patent is extended or adjusted under 35 U.S.C. 154(b) by 0 days.

(21) Appl. No.: 16/602,117

(22) Filed: Aug. 7, 2019

(65) Prior Publication Data

US 2020/0100413 P1 Mar. 26, 2020

(30) Foreign Application Priority Data

Sep. 20, 2018 (JP) ..... PBR 33371

(51) Int. Cl.
*A01H 5/02* (2018.01)
*A01H 6/00* (2018.01)

(52) U.S. Cl.
USPC ..... Plt./236
CPC ..... *A01H 6/00* (2018.05); *A01H 5/02* (2013.01)

(58) Field of Classification Search
USPC ..... Plt./236
CPC ..... A01H 6/00; A01H 5/02
See application file for complete search history.

(56) References Cited

U.S. PATENT DOCUMENTS

PP30,067 P3 1/2019 Koie et al.

*Primary Examiner* — Keith O. Robinson
(74) *Attorney, Agent, or Firm* — Cochran Freund & Young LLC; James Weatherly

(57) ABSTRACT

A new hop plant particularly distinguished by having a cylindrical to club plant shape, an alpha acid content of 8.3%, a ratio content of beta to alpha of 0.58, and a citrus flavor, is disclosed.

2 Drawing Sheets

Genus and species: *Humulus lupulus* L.
Variety denomination: 'Furano 1501U Go'.

CROSS REFERENCE TO RELATED APPLICATION

The present application claims priority to Japan Plant Variety Protection Application No. 33371, as filed on Sep. 20, 2018, the entire contents are herein incorporated by reference for all the application teaches and discloses.

BACKGROUND OF THE NEW PLANT

The present invention comprises a new and distinct variety of Hop, botanically known as *Humulus lupulus* L. and hereinafter referred to by the variety name 'Furano 1501U Go'. 'Furano 1501U Go' is a selection from a controlled cross of the proprietary hop female parent 'Furano Beauty' and the proprietary male parent '070373'.

The proprietary female hop line 'Furano Beauty' and the proprietary male hop line '070373' were cross-pollinated in 2012 in Kamifurano-cho, Sorachi-gun, Hokkaido, Japan and seeds were obtained. The seeds were sown and plants were grown for evaluation. A plant line was selected in March of 2015 in Kamifurano-cho, Sorachi-gun, Hokkaido, Japan and named 'Furano 1501U Go'. In 2015, 'Furano 1501U Go' was first vegetatively propagated in Kamifurano, Hokkaido, Japan via vegetative cuttings. 'Furano 1501U Go' was found to reproduce true to type in successive generations of asexual propagation via vegetative cuttings in Kamifurano, Hokkaido, Japan.

SUMMARY

The following are the most outstanding and distinguishing characteristics of this new variety when grown under normal horticultural practices in Kamifurano, Hokkaido, Japan.

1. Cylindrical to club plant shape;
2. Alpha acid content of 8.3%;
3. Ratio content of beta to alpha of 0.58; and
4. A citrus flavor.

DESCRIPTION OF THE PHOTOGRAPHS

This hop plant is illustrated by the accompanying photographs which show the plant's overall plant shape, leaf shape and cone shape. FIGS. 1-3 are of a four-year-old plant and parts thereof grown in Kamifurano, Hokkaido, Japan in August 2018 while FIG. 2 is also of a four-year-old plant grown in Kamifurano, Hokkaido, Japan taken in June 2018. The colors shown are as true as can be reasonably obtained by conventional photographic procedures.

DESCRIPTION OF THE NEW VARIETY

Figure 1:
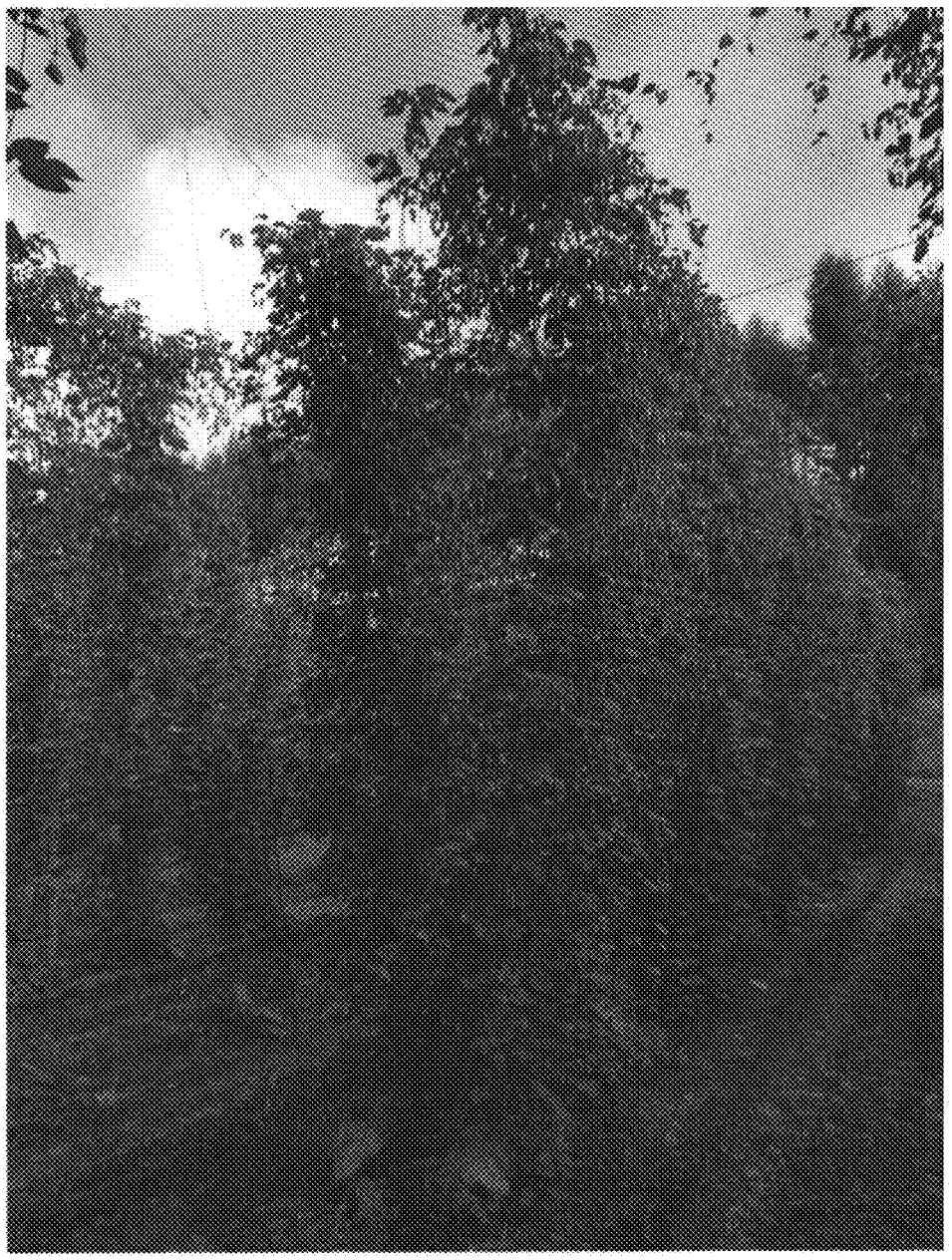
FIG. 1 shows the plant shape of 'Furano 1501U Go'.
Figure 2:
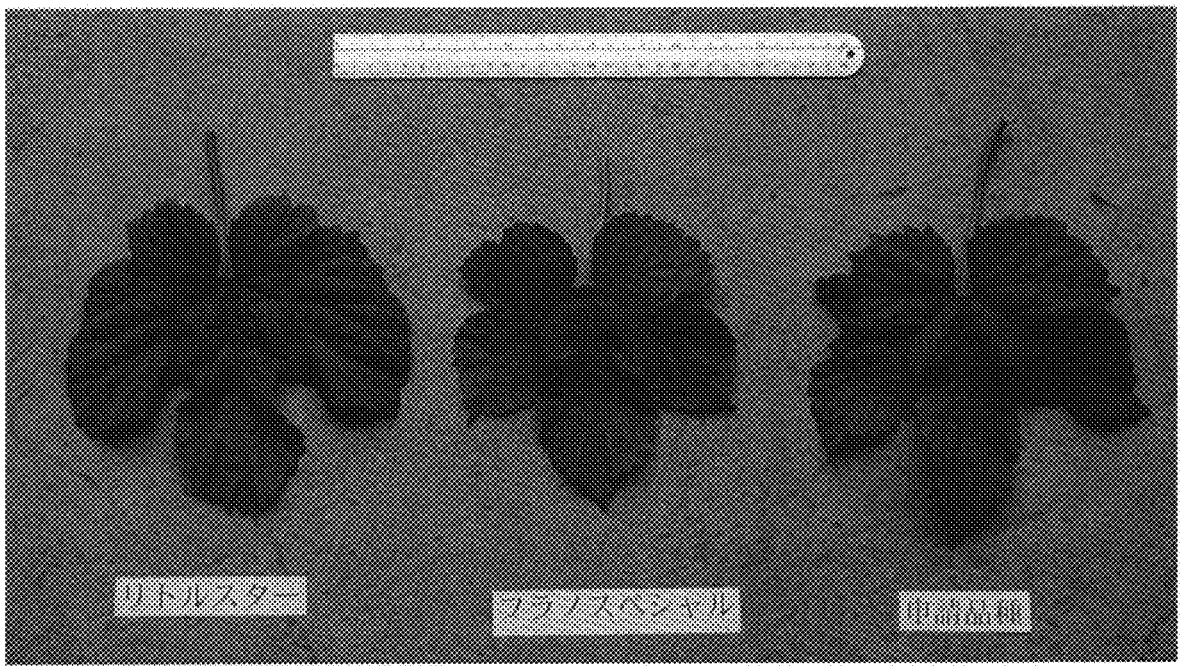
FIG. 2 shows the leaf shape of 'Furano 1501U Go' together with that of 'Little Star' and 'Furano Special' in the left and in the middle, respectively.
Figure 3:
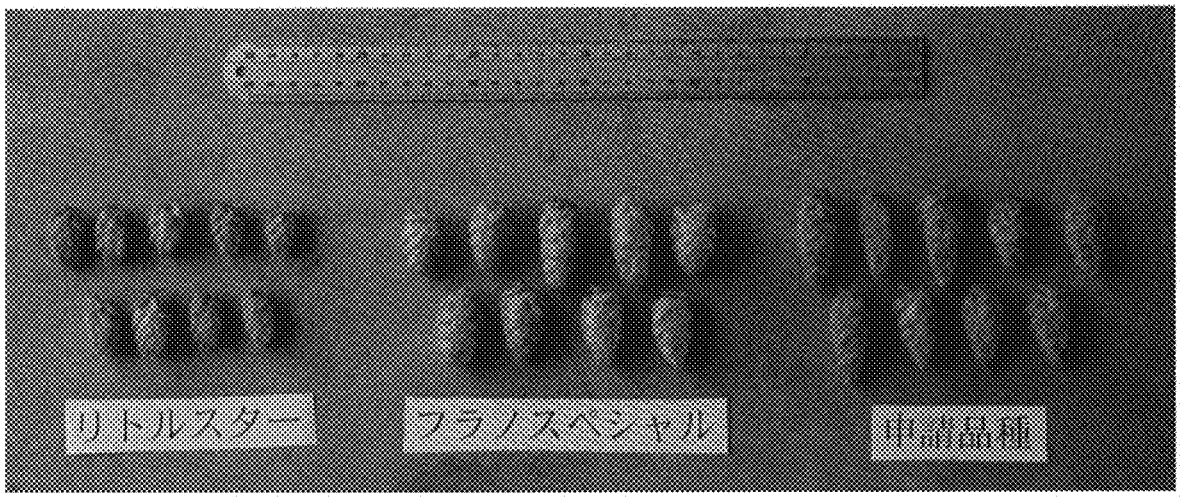
FIG. 3 shows the cone shape of 'Furano 1501U Go' together with that of 'Little Star' and 'Furano Special' in the left and in the middle, respectively.

The following detailed descriptions set forth the distinctive characteristics of 'Furano 1501U Go'. The data, which define these characteristics, were collected from asexual reproductions carried out in Kamifurano, Hokkaido, Japan. Data was collected on 3 to 4-year-old mature plants in Kamifurano, Hokkaido, Japan during the 2017 and 2018 growing season. Color references are to Japan Horticultural Plant Color Chart (1987, Japan Color Research Institute).

Classification:

*Family*.—Cannabaceae.

*Classification*.—*Humulus lupulus* L.

*Common name*.—Hop.

Parents:

*Female parent*.—'Furano Beauty' (unpatented).

*Male parent*.—'070373' (unpatented).

Propagation:

*Type*.—Vegetative cuttings or rhizomes.

Plant description:

*Plant and growth habit*.—The plant growth type is normal, not dwarf.

*Plant shape*.—Cylindrical to club.

*Plant height*.—Hop plants were grown at a trellis of 5.5 m high.

*Plant diameter*.—Two-year-mean diameter of main bine is 9.6 mm, ranges between 8.5 to 11.5 mm.

*Anthocyanin*.—Anthocyanin coloration of the main bine is slightly strong in the end of June.

*Anthocyanin color*.—Soft yellow green (3310) on main bine at maturing.

Lateral branch description:

*Length*.—The length of side shoot at one second of plant is slightly long (2-year mean: 1.30 m, ranges between 0.75 m to 1.65 m); the length of side shoot from upper third of plant is slightly short (2-year mean: 0.84 m, ranges between 0.55 m to 1.30 m).

*Diameter*.—4.0 mm (2-year mean, ranges between 3.0 mm to 5.5 mm).

*Internode length*.—Two-year-mean internode length of side shoot at the middle of the plant height is 23.4 cm.

*Color, fully developed* (*mature*).—Soft yellow green (3310).

*General*.—The density of leaves of side shoot at one second of the plant height is slightly sparse.

Foliage description:

*Arrangement*.—Opposite.

*Length*.—Two-year-mean leaf length is 14.9 cm, ranges between 13.5 mm to 16.5 mm.

*Width*.—Two-year-mean leaf width is 18.4 cm, ranges between 14.5 mm to 21.5 mm.

*Shape*.—Palmate, 3 to 5 lobes.

*Apex*.—Acuminate to acute.

*Base*.—Cordate to hastate.

*Margin*.—Serrate, spiny.

*Texture*.—Upper surface: Blistering of upper side of the blade is slightly weak.

*Venation pattern*.—Palmate.

*Color*.—Fully expanded (mature) leaves: Upper surface: Dark yellow green (3508) to dark green (3716).

Petiole:

*Length*.—Two-year-mean petiole length is 9.9 cm, ranges between 7.5 mm to 12.0 mm.

*Diameter*.—Two-year-mean petiole diameter is 4.0 mm, ranges between 3.0 mm to 5.0 mm.

*General*.—Color of petiole base to bine is grayish purple (9217), but lower half is dull yellow green (3312).

Flower description:

*Flower arrangement and habit*.—Total number of cones of side shoot from middle of plant is slightly low (2-year mean: 44 cones/branch, ranges from 15 to 80); total number of cones of side shoot from upper third of plant is little (2-year mean: 22.0 cones/branch ranges between 7 to 40); number of cones per node of side shoot at one second of plant is slightly little (2-year mean: 7.8 cones/node, ranges between 4.0 to 11.0).

*Time of flowering*.—July 11 to 17 in both 2017 and 2018.

*Time of picking maturity of cones*.—August 25 to 28 in both 2017 and 2018.

Inflorescence buds:

*Description*.—Two-year-mean 100-cone-weight is 26.5 g in dry matter.

*Length*.—Medium (2-year mean: 38.3 mm, ranges between 28.0 mm to 48.0 mm).

*Diameter*.—2-year mean: 38.3 mm, ranges between 28.0 mm to 48.0 mm.

*Shape*.—Narrow ovate.

Spike bracts:

*Length*.—Slightly large (2-year mean: 14.5 mm, ranges between 12.5 mm to 17.0 mm).

*Width*.—Two-year-mean bract width is 10.2 mm, ranges between 7.5 mm to 12.5 mm.

*Shape*.—The width/length ratio is medium (two-year-mean width/length ratio of bracts is 0.7, ranges between 0.5 to 0.9).

*Apex*.—The length of apex of bract is slightly short.

*Degree of opening of bracts*.—Closed.

*Color of cone*.—Slightly dark green, based on UPOV form TG/227/1 (Hop) Characteristics number 20 (UPOV No. 20).

*Margin*.—Entire.

*Color*.—Deep yellowish green (3711) to Strong yellowish green (3710).

Bracteoles:

*Length*.—Two-year-mean length of bracteoles is 12.8 mm, ranges between 10.0 mm to 15.5 mm.

*Width* (*cm*).—Two-year-mean width of bracteoles is 7.5 mm, ranges between 5.5 mm to 10.0 mm).

*Shape*.—Ovate.

*Apex*.—Round.

*Margin*.—Entire.

*Color*.—Strong yellowish green (3710).

Pedicels: Not observed.

Reproductive organs:

*Stamens*.—Not observed.

*Pistils*.—Not observed.

Disease and pest/insect resistance: Not resistant to either downy mildew (*Pseudoperonospora humuli*) or powdery mildew (*Podosphaera macularis*).

Brewing characteristics:

*Alpha acids content in cones.*—8.3% (2-year mean).

*Ratio of beta acids to alpha acids.*—0.58 (2-year mean).

*Ratio of co-alpha to all alpha acids.*—41% (2-year mean).

*Humulene ratio to total oil is.*—49% (2-year mean).

*Caryophyllene ratio to total oil is.*—15% (2-year mean).

*Humulene ration to caryophyllene is.*—3.3 (2-year mean).

*Myrcene ration to total oil is.*—34% (2-year mean).

*Farnesene ration to total oil is.*—0.1% (2-year mean).

*Linalool ration to total oil is.*—0.7% (2-year mean).

*Remaining rate of alpha acids after* 6 months storage at room temperature is.—59.5% (2-year mean).

*Yield per hectare is.*—1.59 t/ha (2018).

*Flavor of "Furano* 1501*U Go" is*.—Citrus.

COMPARISON WITH PARENTAL LINES AND KNOWN VARIETY

'Furano 1501U Go' is a distinct variety of hop. 'Furano 1501U Go' is distinguished from its female parent 'Furano Beauty' and its male parent '070373' as described in Table 1:

TABLE 1

Comparison with Parental Lines

| Characteristic | Variety 'Furano 1501U Go' | Female parent 'Furano Beauty' | Male Parent '070373' |
|---|---|---|---|
| Flower | Produce female flowers and cones | Produce female flowers and cones | Does not produce any cones, but produce male flower |
| Alpha acids in cones | 7.0% to 9.5% | 9.5% to 14.5% | No information |
| Cohumulone ratio to alpha acids | 40% to 41% | 29% to 33% | No information |
| Farnesene ration to total oil | 0.1% | 8.5% to 12.5% | No information |

'Furano 1501U Go' is distinguished from the commercial hop variety 'Furano K906901060 go', commercially named 'Furano Magical' (U.S. Plant Pat. No. 30,067). Differences between the two varieties are described in Table 2:

TABLE 2

Comparison with Similar Variety

| Characteristic | Variety 'Furano 1501U Go' | Commercial line 'Furano K906901060 go' |
|---|---|---|
| Alpha acids in cones | 7.0% to 9.5% | 3.5% to 5.0% |
| Cohumulone ratio to alpha acids | 40% to 41% | 15% to 17.5% |
| Linalool ration to total oil | 0.7% to 0.8% | 1.1% to 2.4% |
| Alpha acids in cones | 7.0% to 9.5% | 3.5% to 5.0% |

We claim:

1. A new and distinct cultivar of Hop plant named 'FURANO 1501U GO' as described and illustrated herein.

* * * * *